(12) United States Patent
Erickson et al.

US007741453B2

(10) Patent No.: US 7,741,453 B2
(45) Date of Patent: Jun. 22, 2010

(54) LONG LASTING FUSION PEPTIDE INHIBITORS FOR HIV INFECTION

(75) Inventors: John W. Erickson, Frederick, MD (US); Dominique P. Bridon, Quebec (CA); Martin Robitaille, Quebec (CA); Grant A. Krafft, Glenview, IL (US); Dong Xie, Germantown, MD (US); Elena Afonina, Frederick, MD (US); Jun Liang, Boyds, MD (US); Sandra DeMeyer, Beerse (BE)

(73) Assignee: Conjuchem Biotechnologies, Inc., Montreal, Quebec (CA)

( * ) Notice: Subject to any disclaimer, the term of this patent is extended or adjusted under 35 U.S.C. 154(b) by 440 days.

(21) Appl. No.: 10/478,811

(22) PCT Filed: May 31, 2002

(86) PCT No.: PCT/CA02/00806

§ 371 (c)(1),
(2), (4) Date: Dec. 10, 2003

(87) PCT Pub. No.: WO02/096935

PCT Pub. Date: Dec. 5, 2002

(65) Prior Publication Data

US 2005/0065075 A1  Mar. 24, 2005

Related U.S. Application Data

(60) Provisional application No. 60/294,241, filed on May 31, 2001.

(51) Int. Cl.
*C08H 1/00* (2006.01)
(52) U.S. Cl. .................................................. 530/402
(58) Field of Classification Search ....................... None
See application file for complete search history.

(56) References Cited

U.S. PATENT DOCUMENTS

| 4,652,629 | A | 3/1987 | Patrick et al. |
| 5,612,034 | A | 3/1997 | Pouletty et al. |
| 5,614,487 | A | 3/1997 | Battersby et al. |
| 5,656,480 | A | 8/1997 | Wild et al. |
| 5,876,969 | A | 3/1999 | Fleer et al. |
| 6,013,263 | A | 1/2000 | Barney et al. |
| 6,017,536 | A | 1/2000 | Barney et al. |
| 6,063,761 | A | 5/2000 | Jones et al. |
| 6,103,236 | A | 8/2000 | Suzawa et al. |
| 6,107,489 | A | 8/2000 | Krantz et al. |
| 6,150,088 | A | 11/2000 | Chan et al. |
| 6,342,225 | B1 | 1/2002 | Jones et al. |
| 6,818,611 | B1 | 11/2004 | Altman |
| 7,090,851 | B1 | 8/2006 | Bridon et al. |
| 7,307,148 | B2 | 12/2007 | Bousquet-Gagnon et al. |
| 2004/0106589 | A1 | 6/2004 | Webb et al. |
| 2005/0065075 | A1 | 3/2005 | Erickson et al. |
| 2005/0070475 | A1 | 3/2005 | Bridon et al. |
| 2006/0099571 | A1 | 5/2006 | Altman |
| 2008/0176794 | A1 | 7/2008 | Bridon et al. |
| 2008/0199483 | A1 | 8/2008 | Bridon et al. |
| 2009/0175821 | A1 | 7/2009 | Bridon et al. |

FOREIGN PATENT DOCUMENTS

| EP | 0 602 290 | 7/1999 |
| EP | 1 264 840 | 12/2002 |
| WO | WO 95/10302 | 4/1995 |
| WO | 9605389 | 2/1996 |
| WO | WO 96/19495 | 6/1996 |
| WO | 9924076 | 5/1999 |
| WO | WO 99/24074 | 5/1999 |
| WO | WO 99/24075 | 5/1999 |
| WO | WO 99/59615 | 5/1999 |
| WO | WO 99/48536 | 10/1999 |
| WO | 0040616 | 7/2000 |
| WO | 0069900 | 11/2000 |
| WO | 0069911 | 11/2000 |
| WO | 0070665 | 11/2000 |
| WO | WO 00/69902 | 11/2000 |
| WO | 0076550 | 12/2000 |
| WO | 0076551 | 12/2000 |
| WO | 0103723 | 1/2001 |
| WO | 0117568 | 3/2001 |
| WO | 0144286 | 6/2001 |

(Continued)

OTHER PUBLICATIONS

Malashkevich, V., Crystal stucture of the simian immunodeficiency virus (SIV) gp41 core: Conseved helical interactions underlie the broad inhibitory acivity of gp41 peptides, Proc. Natl. Acad. Sci. USA, 95:9134-9, 1998.*
Gustchina, E., Differential inhibition of HIV-1 and SIV envelope-mediated cell fusion by C34 peptides derived from the C-terminal heptad repeat of gp41 from diverse strains of HIV-1, HIV-2 and SIV, J. Med. Chem., 48:3036-44, 2005.*
Lambert et al., Peptides from conserved regions of paramyxovirus fusion (F) proteins are potent inhibitors of viral fusion, Proc. Natl. Acad. Sci. USA, 1996, vol. 93, pp. 2186-2191.*
Ito et al., CXCR4-Tropic HIV-1 Suppresses Replication of CCR5-Tropic HIV-1 in Human Lymphoid Tissue by Selective Induction of CC-Chemokines, The Journal of Infectious Diseases, 2004, 189:506-514.*

(Continued)

*Primary Examiner*—Patrick J. Nolan
*Assistant Examiner*—Nicole Kinsey White
(74) *Attorney, Agent, or Firm*—Lando & Anastasi, LLP

(57) ABSTRACT

The present invention relates to C34 peptide derivatives that are inhibitors of viral infection and/or exhibit antifusogenic properties. In particular, this invention relates to C34 derivatives having inhibiting activity against human immunodeficiency virus (HIV), respiratory syncytial virus (RSV), human parainfluenza virus (HPV), measles virus (MeV), and simian immunodeficiency virus (SIV) with long duration of action for the treatment of the respective viral infections.

73 Claims, No Drawings

FOREIGN PATENT DOCUMENTS

| WO | 02096935 | 12/2002 |
|---|---|---|
| WO | 2004028473 | 4/2004 |
| WO | 2004029073 | 4/2004 |
| WO | 2004029201 | 4/2004 |
| WO | 2005007831 | 1/2005 |
| WO | 2005103087 | 11/2005 |
| WO | WO 20058108418 | 11/2005 |
| WO | 2007071068 | 6/2007 |

OTHER PUBLICATIONS

Desrosiers, Prospects for an AIDS vaccine, Nature Medicine, 2004, 10(30):221-223.*
Ji, h., et al. Buried Polar Interactions and Conformational Stability in the Simian Immunodeficiency Viruys (SIV) gp41 Core, Biochemistry 2000, 39:676-685.
International Search Report for PCT/CA02/00806 (6 pgs).
Annex I of Jun. 6, 2005 to Appellant's letter dated Sep. 15, 2004 in EP 00932570.5.
Annex II of Jun. 6, 2005 to Appellant's letter dated Sep. 15, 2004 in EP 00932570.5.
Annexes I, II and III to Appellant's letter dated May 17, 2004 in EP 00932570.5.
Declaration of Serge Saint-Pierre of Sep. 9, 2004 as cited in Opposition of in EP 00932570.5 by Trimeris, Inc.
Declaration of Dominique Bridon, including exhibits, as cited in Opposition of in EP 00932570.5 by Trimeris, Inc.
Declaration of Grant A. Krafft of Jun. 2005 as cited in Opposition of in EP 00932570.5 by Trimeris, Inc.
Baker et al., (1999) "Structural basis for Paramyxovirus-Mediated Membrane Fusion", Mole. Cell., 3, 309-319.
Bressanelli et al., (2004) Embo J., 23, 728-738.
Bridon et al., U.S. Appl. No. 09/623,533, filed Sep. 5, 2000, for "Long-Lasting Antiviral Fusion Inhibitor Peptide Conjugates Comprising BSA and DP-178".
Bullough et al., (1994) "Structure of influenza haemagglutinin at the pH of membrane fusion", Nature, 371, 37-43.
Caffrey et al., (1998) "Three-dimensional solution structure of the 44 kDa ectodomain of SIV gp41" Embo J., 17, 4571-4584.
Chan et al. (1997) Core structure of gp41 from the HIV envelope glycoprotein. Cell 89: 263-273.
Chan et al. (1998) Evidence that a prominent cavity in the coiled coil of HIV type 1 gp41 is an attractive drug target. Proc Natl Acad Sci USA 95: 15613-15617.
Fass et al., (1995) "Dissection of a retrovirus envelope protein reveals structural similarity to influenza hemagglutinin", Curr. Biol. 5, 1377-1383.
Fass et al., (1996) "Retrovirus envelope domain at 1.7 a resolution", Nat. Struct. Biol. 3, 465-469.
Greenberg et al. (2004) Resistance to enfuvirtide, the first HIV fusion inhibitor. J Antimicrob Chemother 54:333-340.
Groenink et al. (1997) "Potent inhibition of replication of primary HIV type 1 isolates in peripheral blood lymphocytes by negatively charged human serum albumins.", AIDS Res Hum Retrovir 13: 179-185.
Hamburger et al. (2005) J Biol Chem 280: 12567-12572.
He et al., "Potent HIV Fusion Inhibitors Against Enfuvirtide-Resistant HIV-1 Strains", PNAS, Oct. 21, 2008. pp. 16332-16337.
Holmes et al. (2000) Site specific 1:1 opioid:albumin conjugate with in vitro activity and long in vivo duration. Bioconj Chem 11: 439-444.
Jacobs et al. (2007) J Biol Chem 282: 32406-32413.
Jansen et al. (1993) "Novel, negatively charged, human serum albumins display potent and selective in vitro anti-human immunodeficiency virus type 1 activity", Mol Pharmacol 44: 1003-1007.
Jetté et al. (2005) "Human growth hormone-releasing factor (hGRF)1-29 albumin bioconjugates activate the GRF receptor on the anterior pituitary in rats: Identification of CJC-1295 as a long-lasting GRF analog," Endocrinology 146: 3052-3058.

Kliger et al., (2000) "Inhibition of HIV-1 entry before gp41 folds into its fusion-active conformation", J Mol Biol 295: 163-168.
Kratz, et al., "Albumin Conjugates of the Anticancer Drug Chlorambucil: Synthesis, Characterization, and in Vitro Efficacy", Arch. Pharm. Pharm. Med. Chem., vol. 331, No. 2, pp. 47-53, 1998.
Kratz, et al., "Preparation, Characterization and in Vitro Efficacy of Albumin Conjugates of Doxorubicin", Biol. Pharm. Bull., vol. 21, No. 1, pp. 56-61, 1998.
Kuiken et al. "HIV Sequence Compendium 2001, Published by Theoretical Biology and Biophysics Group", Los Alamos National Laboratory, 2002: i-viii; 279-466.
Léger et al. (2003) "Synthesis and in vitro analysis of atrial natriuretic peptide-albumin conjugates," Bioorg & Med Chem Lett 13: 3571-3575.
Léger et al. (2004) "Kringle 5 peptide-albumin conjugates with anti-migratory activity", Bioorg & Med. Chem. Lett 14:841-845.
Léger et al. (2004) "Identification of CJC-1131-albumin bioconjugate as a stable and bioactive GLP-1(7-36) analog," Bioorg & Med Chem Lett 14: 4395-4398.
Malashkevich, (1999) Biochemistry, 96. 2662-2667.
Manfredi et al., (2006) Curr Med Chem 13: 2369-2384.
Meanwell et al., (2003) Curr Opinion Drug Disc & Develop 6: 451-461.
Modis et al., (2004) Nature, 427, 313-319.
Muñoz-Barroso et al., (1998) Dilation of the human immunodeficiency virus-1 envelope glycoprotein fusion pore revealed by the inhibitory action of a synthetic peptide from gp41. J Cell Biol 140: 315-23.
Nakamura et al., "Design and Synthesis of Highly Active anti-HIV Peptide based on gp41-C34 Peptide", Peptide Science, Protein Research Foundation, Minoo, JP, Oct. 3, 2001, pp. 73-76.
Olson et al., (2003) Curr Drug Targets-Infectious Disord 3: 283-294.
Otaka et al., (2002) Angew Chem Int Ed Engl 41:2937-2940.
Popovic et al., (1984) Detection, isolation, and continuous production of cytopathic retroviruses (HTLV-III) from patients with AIDS and pre-AIDS. Science 224:497-500.
Porter et al., (2000) Lymphatic transport of proteins after subcutaneous administration. J Pharm Sci 89: 297-310.
Ratner et al. (1985) Complete nucleotide sequence of the AIDS virus, HTLV-III. Nature 313:277-283.
Roman et al. (2003) "Uncommon Mutations at Residue Positions Critical for Enfuvirtide (T-20) Resistance in Enfuvirtide-Naive Patients Infected With Subtype B and Non-B HIV-1 Strains" J. AIDS 33:134-139.
Sougrat et al., (2007) "Electron tomography of the contact between T cells and SIV/HIV-1: Implications for viral entry," PLoS Pathogens 3: 0571-0581.
Stebbing et al., (2004) Where does HIV live? N Engl J Med 350:1872-1880.
Stehle. et al., 1997, "The Loading Rate Determins Tumor Targeting Properties of Methotrexate-Albumin Conjugates in Rats" Anti-Cancer Drugs, (8):677-685.
Stoddart et al. (2007) "Validation of the SCID-hu Thy/Liv mouse model with four classes of licensed antiretrovirals," PLoS ONE 2:e655.
Stoddart., "Albumin-Conjugated C34 Peptide HIV-Fusion Inhibitor: Equipotent to C34 and T-20 in Vitro with Sustained Activity in SCID-HU Thy/Liv Mice", Journal of Biological Chemistry, pp. 1-16, Sep. 22, 2008.
Swart et al. (1996) "Comparative pharmacokinetic, immunologic and hematologic studies on the anti-HIV-1/2 compounds aconitylated and succinylated HAS", J Drug Target 4: 109-116.
Takami, et al. (1992) "Maleylated human serum albumin inhibits HIV-1 infection in vitro." Biochim Biophys Acta 1180: 180-186.
Thibaudeau et al. (2005) Synthesis and evaluation of insulin-human serum albumin conjugates, Bioconj Chem 16: 1000-1008.
Wei et al., (2002) Antimicrob Agents Chemother 64: 1896-1905.
Liu et al., (2005) J Biol Chem 280:11259-11273.
European Search Report for EP 02014617.1 mailed Oct. 25, 2002.
European Search Report for EP 04015696.0 mailed Oct. 6, 2004.
European Search Report for EP 06023309.5 mailed Feb. 16, 2007.
European Search Report for EP 05741050.8 mailed Mar. 27, 2007.

International Search Report for PCT/US00/13651 mailed Oct. 19, 2000.
International Search Report for PCT/CA02/00806 mailed Jul. 10, 2003.
International Search Report for PCT/CA05/00689 mailed Oct. 20, 2005.
International Search Report for PCT/US08/64010 mailed Nov. 25, 2008.
International Search Report for PCT/US08/64016 mailed Nov. 18, 2008.
European Search Report for European Patent Application No. 09009474.9 mailed Sep. 19, 2009.
U.S. Appl. No. 09/623,533, filed Sep. 2000, Bridon et al.
U.S. Appl. No. 09/657,336, filed Sep. 2000, Bridon et al.
U.S. Appl. No. 10/950,010, filed Sep. 24, 2004, Bridon et al.
U.S. Appl. No. 11/579,929, filed Sep. 2007, Bridon et al.
Archakov, Alexander I. et al. (2003) "Protein-Protein Interactions as a Target for Drugs in Proteomics," Proteomics, 3:380-391.
Boeckler, Christophe "Immunogenicity of New Heterobifunctional Cross-Linking Reagants Used in the Conjugation . . . ", Journal of Immunological Methods, (1996), vol. 191:pp. 1-10.
Chen, Chin-Ho et al. (Jun. 1995) "A Molecular Clasp in the Human Immunodeficiency Virus (HIV) Type 1 TM Protein Determines the Anti-HIV Activity of gp41 Derivatives: Implication for Viral Fusion," Journal of Virology, 69(6): 3771-3777.
Christodoulou, John et al. "H NMR of albumin in human blood plasma: drug binding and redox reactions at $Cys^{34}$", FEBS Letters 376:pp. 1-5 (1995).
Davies, David R. et al. (Jan. 1996) "Interactions of Protein Antigens with Antibodies," Proc. Natl. Acad. Sci. USA, 93:7-12.
Jiang, Shibo et al. (2002) "Peptide and Non-peptide HIV Fusion Inhibitors," Current Pharmaceutical Design, 8:563-580.
Jones, Susan et al. (Jan. 1996) "Principles of Protein-Protein Interactions," Proc. Natl. Acad. Sci. USA, 93:13-20.
Kwong, Peter D. et al. (Feb. 2000) "Oligomeric Modeling and Electrostatic Analysis of the gp120 Envelope Glycoprotein of Human Immunodeficiency Virus," Journal of Virology, 74(4):1961-1972.
Labrijn, Aran F. "Access of Antibody Molecules to the Conserved Coreceptor Binding Site of Glycoprotein gp120 . . . " Journal of Virology, (Oct. 2003), vol. 77:pp. 10557-10565.
Lamber, D.M. et al. "Peptides from conserved regions of paramyxovirus fusion (F) proteins are potent inhibitors of viral fusion", (Nov. 1995) Medical Sciences, pp. 2186-2191.
Lawless, Mary K. et al. (1996) "HIV-1 Membrane Fusion Mechanism: Structural Studies of the Interactions between Biologically-Active Peptides from gp41," Biochemistry, 35: 13697-13708.
Narazaki, Ryuichi, et al. "Covalent Binding Between Bucillamine Derivatives and Human Serum Albumin" Pharmaceutical Research, vol. 13, No. 9: pp. 1317-1321 (1996).
Qureshi, Nasar M. "Characterization of a Putative Cellular Receptor for HIV-1 Transmembrane Glycoprotein Using Synthetic Peptides" AIDS, (1990) vol. 4:pp. 553-558.
Sanders, Rogier W. et al. (Sep. 2002) "Stabilization of the Soluble, Cleaved, Trimeric Form of the Envelope Glycoprotein Complex of Human Immunodeficiency Virus Type 1," Journal of Virology, 76(17) 8875-8889.
Shugars, Diane C. et al. (May 1996) "Biophysical Characterization of Recombinant Proteins Expressing the Leucine Zipper-Like Domain of the Human Immunodeficiency Virus Type 1 Transmembrane Protein gp41," Journal of Virology, 70(5): 2982-2991.
Sodroski, Joseph G. "HIV-1 Entry Inhibitors in the Side Pocket", Cell, (Oct. 29, 1999), vol. 99:pp. 243-246.
Tolman, R.L. et al. (1993) "Cyclic V3-Loop-Related HIC-1 Conjugate Vaccines: Synthesis, Conformation and Immunological Properties" Int. J. Peptide Protein Res. 41:455-466.
Wang, Ning et al. (Apr. 1995) "Sequence Diversity of V1 and V2 Domains of gp120 from Human Immunodeficiency Virus Type 1: Lack of Correlation with Viral Phenotype," Journal of Virology, 69(4): 2708-2715.
Wild, Carl "A synthetic Peptide inhibitor of Human Immunodeficiency Virus Replication: Correlation . . . ", Proc. Natl. Acad. Sci., (Nov. 1992) vol. 89:pp. 10537-10541.
Yang, Xinzhen et al. (May 2000) "Modifications that Stabilize Human Immunodeficiency Virus Envelope Glycoprotein Trimers in Solution," Journal of Virology, 74(10): 4746-4754.
Decision from Appeal Board dated Jul. 27, 2007.
Decision from Opposition Division dated Feb. 1, 2005.
Jiang et al. (2000) A Convenient Cell Fusion Assay for Rapid Screening for HIV Entry Inhibitors, Proc. SPIE 3926: 212-219.
Kliger et al. (2001) Mode of Action of an Antiviral Peptide from HIV-1, J Biol Chem 276:1391-1397.
Popovic et al., (1984) T4 positive human neoplastic cell lines susceptible to and permissive for HTLV-III. Lancet ii:1472-1473.
Yang et al. (1999) J. Struct. Biol. 126, 131-144.
US 6,020,459, 02/2000, Barney et al. (withdrawn)

* cited by examiner

SEQUENCE LISTING

```
<160> NUMBER OF SEQ ID NOS: 9

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Derivatized lysine connected to a 2-(2-
      amino)ethoxy)]ethoxy acetic acid (AEEA) linked to maleimido
      propionic acid (MPA)
<220> FEATURE:
<223> OTHER INFORMATION: C-term amidated

<400> SEQUENCE: 2

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Xaa Asn Glu Gln Glu
            20                  25                  30

Leu Leu

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Derivatized lysine connected to a 2-(2-
      amino)ethoxy)]ethoxy acetic acid (AEEA) linked to maleimido
      propionic acid (MPA)
<220> FEATURE:
<223> OTHER INFORMATION: C-term amidated

<400> SEQUENCE: 3

Trp Met Glu Trp Asp Arg Glu Ile Asn Asn Tyr Thr Xaa Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 4
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Derivatized lysine connected to a 2-(2-
      amino)ethoxy)]ethoxy acetic acid (AEEA) linked to maleimido
      propionic acid (MPA)
<220> FEATURE:
<223> OTHER INFORMATION: C-term amidated

<400> SEQUENCE: 4

Trp Met Glu Trp Asp Arg Glu Ile Asn Xaa Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Derivatized lysine connected to a 2-(2-
      amino)ethoxy)]ethoxy acetic acid (AEEA) linked to maleimido
      propionic acid (MPA)
<220> FEATURE:
<223> OTHER INFORMATION: C-term amidated

<400> SEQUENCE: 5

Trp Met Glu Trp Asp Arg Glu Ile Xaa Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 6
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Derivatized lysine linked to maleimido
      propionic acid (MPA)
<220> FEATURE:
<223> OTHER INFORMATION: C-term amidated

<400> SEQUENCE: 6

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Xaa
        35
```

```
<210> SEQ ID NO 7
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Derivatized lysine connected to a 2-(2-
      amino)ethoxy]ethoxy acetic acid (AEEA) linked to maleimido
      propionic acid (MPA)
<220> FEATURE:
<223> OTHER INFORMATION: C-term amidated

<400> SEQUENCE: 7

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Xaa
        35

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Derivatized tryptophan connected to a maleimido
      propionic acid (MPA)
<220> FEATURE:
<223> OTHER INFORMATION: C-term amidated

<400> SEQUENCE: 8

Xaa Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Derivatized tryptophan connected to a 2-(2-
      amino)ethoxy)] ethoxy acetic acid (AEEA) linked to maleimido
      propionic acid (MPA)
<220> FEATURE:
<223> OTHER INFORMATION: C-term amidated

<400> SEQUENCE: 9

Xaa Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu
```

LONG LASTING FUSION PEPTIDE INHIBITORS FOR HIV INFECTION

FIELD OF INVENTION

This invention relates to C34 peptide derivatives that are inhibitors of viral infection and/or exhibit antifusogenic properties. In particular, this invention relates to C34 derivatives having inhibiting activity against human immunodeficiency virus (HIV), respiratory syncytial virus (RSV), human parainfluenza virus (HPV), measles virus (MeV), and simian immunodeficiency virus (SIV) with long duration of action for the treatment of the respective viral infections.

SEQUENCE LISTING

The instant application contains a Sequence Listing which has been submitted via EFS-Web and is hereby incorporated by reference in its entirety. Said ASCII copy, created on Dec. 21, 2009, is named C2077700.txt, and is 6,094 bytes in size.

BACKGROUND OF THE INVENTION

Membrane fusion events, while commonplace in normal cell biological processes, are also involved in a variety of disease states, including, for example the entry of enveloped viruses into cells. Peptides are known to inhibit or otherwise disrupt membrane fusion-associated events, including, for example, inhibiting retroviral transmission to uninfected cells.

HIV is a member of the lentivirus family of retroviruses, and there are two prevalent types of HIV, HIV-1 and HIV-2, with various strain of each having been identified. HIV targets CD4+ cells, and viral entry depends on binding of the HIV protein gp120 to the CD4 glycoprotein and a chemokine receptor on cell surface. C34 is known to exhibit anti-viral activity against HIV, including inhibiting CD4+ cell infection by free virus and/or inhibiting HIV-induced syncytia formation between infected and uninfected CD4+ cells. The inhibition is believed to occur by binding of C34 to the first heptad repeat region in gp41 and thus preventing the first and second heptad repeat regions from formating the fusigenic hairpin structure.

C34 is known to possess antifusogenic activity, i.e., it has the ability to inhibit or reduce the level of membrane fusion events between two or more entities, e.g., virus-cell or cell-cell, relative to the level of membrane fusion that occurs in the absence of the peptide. More specifically, WO 00/06599 teaches the use of C34 to inactivate gp41, and thus, prevent or reduce HIV-1 entry into cells.

While many of the anti-viral or anti-fusogenic peptides described in the art exhibit potent anti-viral and/or anti-fusogenic activity, C34, like all such peptides, suffers from short half-life in vivo, primarily due to rapid serum clearance and peptidase and protease activity. This in turn greatly reduces its effective anti-viral activity.

There is therefore a need for a method of prolonging the half-life of peptides like C34 in vivo without substantially affecting the anti-fusogenic activity.

SUMMARY OF THE INVENTION

In accordance with the present invention, there is now provided C34 peptide derivatives having an extended in vivo half-life when compared with the corresponding unmodified C34 peptide sequence. More specifically, the present invention is concerned with compounds of Formulae I-VIII illustrated below, which are capable of reacting with thiol groups on a blood component, either in vivo or ex vivo, to form a stable covalent bond. Formulae I-VIII disclose SEQ ID NOS 2, 3, 4, 5, 6, 7, 8 and 9, respectively, in order of appearance.

-continued
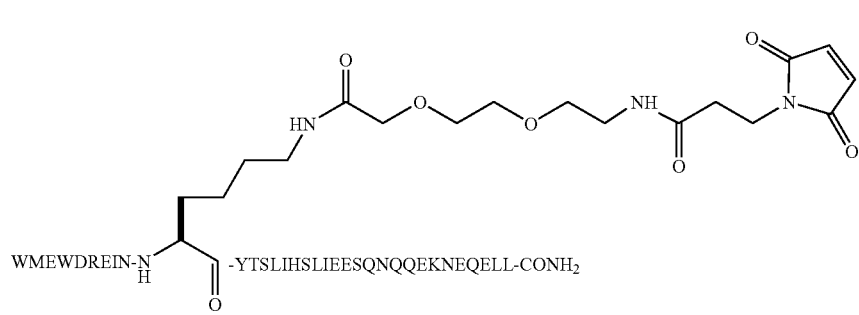
III
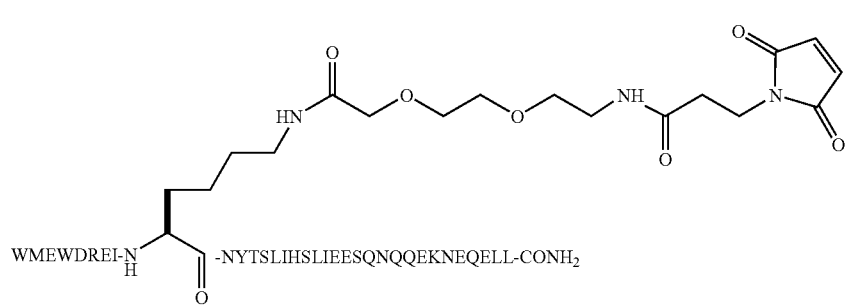
IV
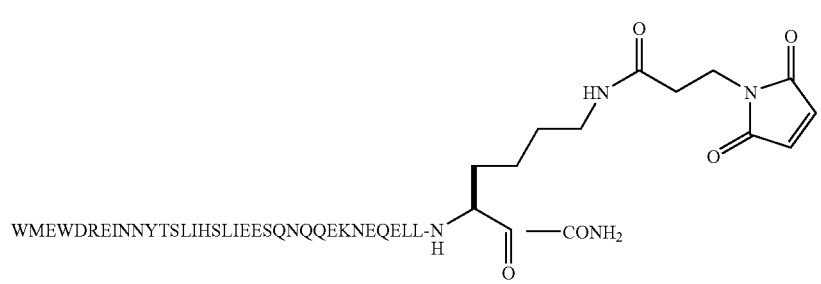
V
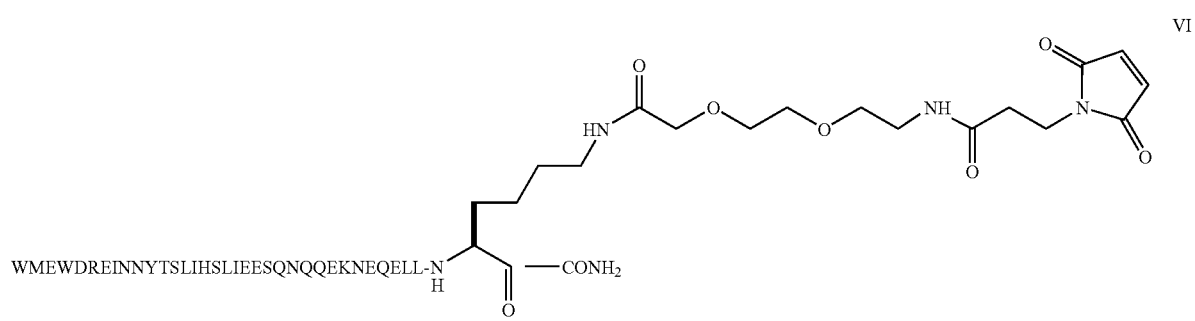
VI
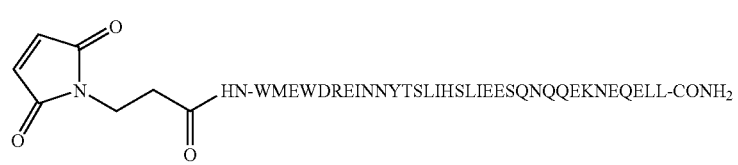
VII
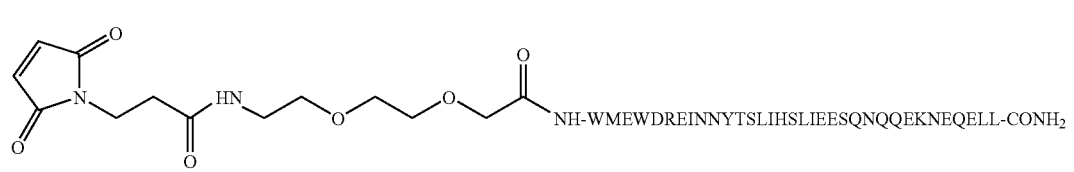
VIII Preferred blood components comprise proteins such as immunoglobulins, including IgG and IgM, serum albumin, ferritin, steroid binding proteins, transferrin, thyroxin binding protein, α-2-macroglobulin etc., serum albumin and IgG being more preferred, and serum albumin being the most preferred.

In another aspect of the invention, there is provided a pharmaceutical composition comprising the derivatives of Formulae I-VII in combination with a pharmaceutically acceptable carrier. Such composition is useful for inhibiting the activity of HIV, RSV, HPV, MeV or SIV.

In a further embodiment of the present invention, there is provided a method for inhibiting the activity of HIV, RSV, HPV, MeV or SIV. The method comprises administering to a subject, preferably a mammal, an effective amount of the compounds of Formulae I-VIII or a conjugate thereof, alone or in combination with a pharmaceutical carrier.

In a further aspect of the present invention, there is provided a conjugate comprising the compounds of Formulae I-VIII covalently bonded to a blood component.

In a further aspect of the present invention, there is provided a method for extending the in vivo half-life of the C34 peptide in a subject, the method comprising covalently bonding the compounds of Formulae I-VIII to a blood component.

DETAILED DESCRIPTION OF THE INVENTION

The present invention meets these and other needs and is directed to C34 peptides derivatives of Formulae I-VIII having anti-viral activity and/or anti-fusogenic activity. These C34 peptides derivatives provide for an increased stability in vivo and a reduced susceptibility to peptidase or protease degradation. As a result, the compounds of Formulae I-VIII minimize the need for more frequent, or even continual, administration of the peptides. The present C34 derivatives can be used, e.g., as a prophylactic against and/or treatment for infection of a number of viruses, including human immunodeficiency virus (HIV), human respiratory syncytial virus (RSV), human parainfluenza virus (HPV), measles virus (MeV) and simian immunodeficiency virus (SIV).

The modification made to the native C34 peptide sequence allows it to react with available thiol groups on blood components to form stable covalent bonds. In one embodiment of the invention, the blood component comprises a blood protein, including a mobile blood protein such as albumin, which is most preferred.

The compounds of Formulae I-VIII inhibit viral infection of cells, by, for example, inhibiting cell-cell fusion or free virus infection. The route of infection may involve membrane fusion, as occurs in the case of enveloped or encapsulated viruses, or some other fusion event involving viral and cellular structures.

The blood components to which the present anti-viral C34 derivatives covalently bonds may be either fixed or mobile. Fixed blood components are non-mobile blood components and include tissues, membrane receptors, interstitial proteins, fibrin proteins, collagens, platelets, endothelial cells, epithelial cells and their associated membrane and membraneous receptors, somatic body cells, skeletal and smooth muscle cells, neuronal components, osteocytes and osteoclasts and all body tissues especially those associated with the circulatory and lymphatic systems. Mobile blood components are blood components that do not have a fixed situs for any extended period of time, generally not exceeding 5 minutes, and more usually one minute. These blood components are not membrane-associated and are present in the blood for extended periods of time in a minimum concentration of at least 0.1 μg/ml. Mobile blood components include serum albumin, transferrin, ferritin and immunoglobulins such as IgM and IgG. The half-life of mobile blood components is at least about 12 hours.

Protective groups may be required during the synthesis process of the present C34 derivative. These protective groups are conventional in the field of peptide synthesis, and can be generally described as chemical moieties capable of protecting the peptide derivative from reacting with other functional groups. Various protective groups are available commercially, and examples thereof can be found in U.S. Pat. No. 5,493,007 which is hereby incorporated by reference. Typical examples of suitable protective groups include acetyl, fluorenylmethyloxycarbonyl (FMOC), t-butyloxycarbonyl (BOC), benzyloxycarbonyl (CBZ), etc. In addition, Table 1 provides both the three letter and one letter abbreviations for amino acids.

TABLE 1

NATURAL AMINO ACIDS AND THEIR ABBREVIATIONS

| Name | 3-letter abbreviation | 1-letter abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present C34 derivatives may be administered in vivo such that conjugation with blood components occurs in vivo, or they may be first conjugated to blood components in vitro and the resulting conjugated derivative administered in vivo.

The present invention takes advantage of the properties of existing anti-viral and antifusogenic peptides. The viruses that may be inhibited by the peptides include, but are not limited to all strains of viruses listed, e.g., in U.S. Pat. Nos. 6,013,263 and 6,017,536 at Tables V-VII and IX-XIV therein. These viruses include, e.g., human retroviruses, including HIV-1, HIV-2, and human T-lympocyte viruses (HTLV-I and HTLV-II), and non-human retroviruses, including bovine leukosis virus, feline sarcoma virus, feline leukemia virus, simian immunodeficiency virus (SIV), simian sarcoma virus, simian leukemia, and sheep progress pneumonia virus. Non-retroviral viruses may also be inhibited by the present C34 derivatives, including human respiratory syncytial virus (RSV), canine distemper virus, Newcastle Disease virus, human parainfluenza virus (HPIV), influenza viruses, measles viruses (MeV), Epstein-Barr viruses, hepatitis B viruses, and simian Mason-Pfizer viruses. Non-enveloped viruses may also be inhibited by the present C34 derivatives, and include, but are not limited to, picomaviruses such as polio viruses, hepatitis A virus, enteroviruses, echoviruses, coxsackie viruses, papovaviruses such as papilloma virus, parvoviruses, adenoviruses, and reoviruses.

The focus of the present invention is to modify the C34 peptide sequence to confer to this peptide improved bioavailability, extended half-life and better distribution through selective conjugation of the peptide onto a protein carrier without substantially modifying the peptide's anti-viral properties. The carrier of choice (but not limited to) for this invention would be albumin conjugated through its free thiol.

The present C34 derivatives are designed to specifically react with thiol groups on mobile blood proteins. Such reaction is established by covalent bonding of the peptide modified with a maleimide link to a thiol group on a mobile blood protein such as serum albumin or IgG.

Thiol groups being less abundant in vivo than, for example, amino groups, the maleimide-modified C34 peptide of the present invention, will covalently bond to fewer proteins. For example, in albumin (the most abundant blood protein) there is only a single thiol group. Thus, a C34-maleimide-albumin conjugate will tend to comprise approximately a 1:1 molar ratio of C34 peptide to albumin. In addition to albumin, IgG molecules (class U) also have free thiols. Since IgG molecules and serum albumin make up the majority of the soluble protein in blood they also make up the majority of the free thiol groups in blood that are available to covalently bond to the C34 peptide derivative.

Further, even among free thiol-containing blood proteins, including IgGs, specific labeling with a maleimide leads to the preferential formation of a C34-maleimide-albumin conjugate due to the unique characteristics of albumin itself. The single free thiol group of albumin, highly conserved among species, is located at amino acid residue 34 ($Cys^{34}$). It has been demonstrated recently that the $Cys^{34}$ of albumin has increased reactivity relative to free thiols on other free thiol-containing proteins. This is due in part to the very low pK value of 5.5 for the $Cys^{34}$ of albumin. This is much lower than typical pK values for cysteine residues in general, which are typically about 8. Due to this low pK, under normal physiological conditions $Cys^{34}$ of albumin is predominantly in the ionized form, which dramatically increases its reactivity. In addition to the low pK value of $Cys^{34}$, another factor which enhances the reactivity of $Cys^{34}$ is its location, which is in a hydrophobic pocket close to the surface of one loop of region V of albumin. This location makes $Cys^{34}$ very available to ligands of all kinds, and is an important factor in $Cys^{34}$'s biological role as free radical trap and free thiol scavenger. These properties make $Cys^{34}$ highly reactive with maleimide-C34, and the reaction rate acceleration can be as much as 1000-fold relative to rates of reaction of maleimide-C34 with other free-thiol containing proteins.

Another advantage of C34-maleimide-albumin conjugates is the reproducibility associated with the 1:1 loading of C34 to albumin specifically at $Cys^{34}$. Other techniques, such as glutaraldehyde, DCC, EDC and other chemical activations of, e.g, free amines, lack this selectivity. For example, albumin contains 52 lysine residues, 25-30 of which are located on the surface of albumin and therefore accessible for conjugation. Activating these lysine residues, or alternatively modifying C34 to couple through these lysine residues, results in a heterogenous population of conjugates. Even if 1:1 molar ratios of C34 to albumin are employed, the yield will consist of multiple conjugation products, some containing 0, 1, 2 or more C34 per albumin, and each having C34 randomly coupled at any one or more of the 25-30 available lysine sites. Given the numerous possible combinations, characterization of the exact composition and nature of each conjugate batch becomes difficult, and batch-to-batch reproducibility is all but impossible, making such conjugates less desirable as a therapeutic. Additionally, while it would seem that conjugation through lysine residues of albumin would at least have the advantage of delivering more therapeutic agent per albumin molecule, studies have shown that a 1:1 ratio of therapeutic agent to albumin is preferred. In an article by Stehle, et al., "The Loading Rate Determines Tumor Targeting properties of Methotrexate-Albumin Conjugates in Rats," *Anti-Cancer Drugs*, Vol. 8, pp. 677-685 (1988), incorporated herein in its entirety, the authors report that a 1:1 ratio of the anti-cancer methotrexate to albumin conjugated via glutaraldehyde gave the most promising results. These conjugates were preferentially taken up by tumor cells, whereas conjugates bearing 5:1 to 20:1 methotrexate molecules had altered HPLC profiles and were quickly taken up by the liver in vivo. It is postulated that at these higher ratios, conformational changes to albumin diminish its effectiveness as a therapeutic carrier.

Through controlled administration of the present C34 derivatives in vivo, one can control the specific labeling of albumin and IgG in vivo. In typical administrations, 80-90% of the administered C34 derivatives will label albumin and less than 5% will label IgG. Trace labeling of free thiols such as glutathione will also occur. Such specific labeling is preferred for in vivo use as it permits an accurate calculation of the estimated half-life of C34.

In addition to providing controlled specific in vivo labeling, the present C34 derivatives can provide specific labeling of serum albumin and IgG ex vivo. Such ex vivo labeling involves the addition of the C34 derivatives to blood, serum or saline solution containing serum albumin and/or IgG. Once conjugation has occurred ex vivo with the C34 derivative, the blood, serum or saline solution can be readministered to the patient's blood for in vivo treatment, or lyophilized.

The present C34 derivatives may be synthesized by standard methods of solid phase peptide chemistry well known to any one of ordinary skill in the art. For example, the peptide may be synthesized by solid phase chemistry techniques following the procedures described by Steward et al. in *Solid Phase Peptide Synthesis,* 2nd Ed., Pierce Chemical Company, Rockford, Ill., (1984) using a Rainin PTI Symphony synthesizer. Similarly, peptides fragments may be synthesized and subsequently combined or linked together to form the C34 peptide sequence (segment condensation).

For solid phase peptide synthesis, a summary of the many techniques may be found in Stewart et al. in "*Solid Phase Peptide Synthesis*", W. H. Freeman Co. (San Francisco), 1963 and Meienhofer, *Hormonal Proteins and Peptides,* 1973, 2 46. For classical solution synthesis, see for example Schroder et al. in "*The Peptides*", volume 1, Acacemic Press (New York). In general, such method comprise the sequential addition of one or more amino acids or suitably protected amino acids to a growing peptide chain on a polymer. Normally, either the amino or carboxyl group of the first amino acid is protected by a suitable protecting group. The protected and/or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

After all the desired amino acids have been linked in the proper sequence, any remaining protecting groups (and any solid support) are cleaved sequentially or concurrently to afford the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing the present C34 derivatives involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Examples of N-protecting groups and carboxy-protecting groups are disclosed in Greene, "Protective Groups In Organic Synthesis," (John Wiley & Sons, New York pp. 152-186 (1981)), which is hereby incorporated by reference. Examples of N-protecting groups comprise, without limitation, loweralkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxy-acetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl, o-nitrophenylsulfonyl, 2,2,5,7,8-pentamethylchroman-6-sulfonyl (pmc), and the like; carbamate forming groups such as t-amyloxycarbonyl, benzyloxycarbonyl, p-chlorobenzyloxycarbonyl, p-methoxy-benzyloxycarbonyl, p-nitrobenzyloxycarbonyl, 2-nitrobenzyloxycarbonyl, p-bromoenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxy-benzyloxycarbonyl, 3,4,5-trimethoxybenzyloxycarbonyl, 1-(p-biphenylyl)-1-methylthoxycarbonyl, α,α-dimethyl-3,5-dimethoxybenzyloxycarbonyl, benzhydryloxycarbonyl, t-butyloxycarbonyl (boc), diisopropylmethoxycarbonyl, isopropyloxycarbonyl, ethoxycarbonyl, methoxycarbonyl, allyloxycarbonyl, 2,2,2,-trichloroethoxycarbonyl, phenoxy-carbonyl, 4-nitrophenoxycarbonyl, fluorenyl-9-methoxycarbonyl, isobornyloxycarbonyl, cyclopentyloxycarbonyl, adamantyloxycarbonyl, cyclohexyloxycarbonyl, phenylthiocarbonyl and the like; arylalkyl groups such as benzyl, biphenylisopropyloxycarbonyl, triphenylmethyl, benzyloxymethyl, 9-fluorenylmethyloxycarbonyl (Fmoc) and the like and silyl groups such as trimethylsilyl and the like. Preferred α-N-protecting group are o-nitrophenylsulfenyl; 9-fluorenylmethyl oxycarbonyl; t-butyloxycarbonyl (boc), isobornyloxycarbonyl; 3,5-dimethoxybenzyloxycarbonyl; t-amyloxycarbonyl; 2-cyano-t-butyloxycarbonyl, and the like, 9-fluorenyl-methyloxycarbonyl (Fmoc) being more preferred, while preferred side chain N-protecting groups comprise 2,2,5,7,8-penta-methyl-chroman-6-sulfonyl (pmc), nitro, p-toluenesulfonyl, 4-methoxybenzene-sulfonyl, Cbz, Boc, and adamantyloxycarbonyl for side chain amino groups like lysine and arginine; benzyl, o-bromobenzyloxycarbonyl, 2,6-dichlorobenzyl, isopropyl, t-butyl (t-Bu), cyclohexyl, cyclopenyl and acetyl (Ac) for tyrosine; t-butyl, benzyl and tetrahydropyranyl for serine; trityl, benzyl, Cbz, p-toluenesulfonyl and 2,4-dinitrophenyl for histidine; formyl for tryptophan; benzyl and t-butyl for aspartic acid and glutamic acid; and triphenylmethyl (trityl) for cysteine.

A carboxy-protecting group conventionally refers to a carboxylic acid protecting ester or amide group. Such carboxy protecting groups are well known to those skilled in the art, having been extensively used in the protection of carboxyl groups in the penicillin and cephalosporin fields as described in U.S. Pat. No. 3,840,556 and U.S. Pat. No. 3,719,667, the disclosures of which are hereby incorporated herein by reference. Representative carboxy protecting groups comprise, without limitation, $C_1$-$C_8$ loweralkyl; arylalkyl such as phenethyl or benzyl and substituted derivatives thereof such as alkoxybenzyl or nitrobenzyl groups; arylalkenyl such as phenylethenyl; aryl and substituted derivatives thereof such as 5-indanyl; dialkylaminoalkyl such as dimethylaminoethyl; alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl; cycloalkanoyloxyalkyl groups such as cyclopropylcarbonyloxymethyl, cyclobutylcarbonyloxymethyl, cyclo-pentylcarbonyloxymethyl, cyclohexylcarbonyloxymethyl; aroyloxyalkyl such as benzoyloxymethyl, benzoyloxyethyl; arylalkylcarbonyloxyalkyl such as benzylcarbonyloxymethyl, 2-benzylcarbonyloxyethyl; alkoxycarbonylalkyl or cycloalkyloxycarbonylalkyl such as methoxycarbonylmethyl, cyclohexyloxycarbonylmethyl, 1-methoxyarbonyl-1-ethyl; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl; aryloxycarbonyloxyalkyl such as 2-(phenoxycarbonyloxy)ethyl, 2-(5-indanyloxycarbonyloxy)-ethyl; alkoxyalkylcarbonyl-oxyalkyl such as 2-(1-methoxy-2-methylpropan-2-oyloxy)-ethyl; arylalkyloxycarbonyl-oxyalkyl such as 2-(benzyloxycarbonyloxy)ethyl; arylalkenyloxycarbonyloxyalkyl such as 2-(3-phenylpropen-2-yloxycarbonyloxy)ethyl; alkoxycarbonylaminoalkyl such as t-butyloxycarbonylaminomethyl; alkylaminocarbonylaminoalkyl such as methylamino-carbonylaminomethyl; alkanoylaminoalkyl such as acetylaminomethyl; heterocyclic-carbonyloxyalkyl such as 4-methylpiperazinyl-carbonyloxymethyl; dialkylamino-carbonylalkyl such as dimethylaminocarbonylmethyl, diethylaminocarbonylmethyl; (5-(loweralkyl)-2-oxo-1,3-dioxolen-4-yl)alkyl such as (5-t-butyl-2-oxo-1,3-dioxolen-4-yl)methyl; and (5-phenyl-2-oxo-1,3-dioxolen-4-yl)alkyl such as (5-phenyl-2-oxo-1,3-dioxolen-4-yl)methyl. Representative amide carboxy protecting groups comprise, without limitation, aminocarbonyl and loweralkylaminocarbonyl groups. Of the above carboxy-protecting groups, loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester are preferred. Preferred amide carboxy protecting groups are loweralkylamino-carbonyl groups.

In the solid phase peptide synthesis method, the α-C-terminal amino acid is attached to a suitable solid support or resin. Suitable solid supports useful for the above synthesis are those materials that are inert to the reagents and reaction conditions of the stepwise condensation-deprotection reactions, as well as being insoluble in the media used. The preferred solid support for synthesis of α-C-terminal carboxy peptides is 4-hydroxymethylphenoxyacetyl-4'-methylbenzyhydrylamine resin (HMP resin). The preferred solid support for α-C-terminal amide peptides is an Fmoc-protected Ramage resin, manufactured and sold by Bachem Inc., California.

At the end of the solid phase synthesis, the peptide is removed from the resin and deprotected, either in successive operations or in a single operation. Removal of the peptide and deprotection can be accomplished conventionally in a single operation by treating the resin-bound polypeptide with a cleavage reagent comprising thioanisole, triisopropyl silane, phenol, and trifluoroacetic acid. In cases wherein the α-C-terminal of the peptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage mixture described above. The fully deprotected peptide can be purified by a sequence of chromatographic steps employing any or all of the following types: ion exchange on a weakly basic resin (acetate form); hydrophobic adsorption chromatography on underivatized polystyrene-divinylbenzene (such as Amberlite XAD™); silica gel adsorption chromatography, ion exchange chromatography on carboxymethylcellulose; partition chromatography, e.g. on Sephadex G25™, LH-20™ or countercurrent distribution; high performance liquid chromatography (HPLC), especially reverse-phase HPLC on octyl- or phenyl/hexylsilyl-silica bonded phase column packing. Anyone of ordinary skill in the art will be able to determine easily what would be the preferred chromatographic steps or sequences required to obtain acceptable purification of the C34 peptide.

Molecular weights of these peptides are determined using Electrospray mass spectroscopy.

The present C34 derivatives may be used alone or in combination to optimize their therapeutic effects. They can be administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The C34 derivatives may be administered parenterally, such as intravascularly (IV), intraarterially (IA), intramuscularly (IM), subcutaneously (SC), or the like. Administration may in appropriate situations be by transfusion. In some instances, where reaction of the functional group is relatively slow, administration may be oral, nasal, rectal, transdermal or aerosol, where the nature of the conjugate allows for transfer to the vascular system. Usually a single injection will be employed although more than one injection may be used, if desired. The peptide derivative may be administered by any convenient means, including syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g., intravenously, peripheral or central vein. Other routes may find use where the administration is coupled with slow release techniques or a protective matrix. The intent is that the C34 derivative be effectively distributed in the blood, so as to be able to react with the blood components. The concentration of the conjugate will vary widely, generally ranging from about 1 pg/ml to 50 mg/ml. The total administered intravascularly will generally be in the range of about 0.1 mg/ml to about 10 mg/ml, more usually about 1 mg/ml to about 5 mg/ml.

By bonding to long-lived components of the blood, such as immunoglobulin, serum albumin, red blood cells and platelets, a number of advantages ensue. The activity of the C34 derivatives is extended for days to weeks. Only one administration need to be given during this period of time. Greater specificity can be achieved, since the active compound will be primarily bound to large molecules, where it is less likely to be taken up intracellularly to interfere with other physiological processes.

The formation of the covalent bond between the blood component may occur in vivo or ex vivo. For ex vivo covalent bond formation, the C34 derivative is added to blood serum or a saline solution containing purified blood components such as human serum albumin or IgG, to permit covalent bond formation between the derivative and the blood component. In a preferred format, the C34 derivative is reacted with human serum albumin in saline solution. After formation of the conjugate, the latter may be administered to the subject or lyophilized.

The blood of the mammalian host may be monitored for the activity of the C34 peptide and/or presence of the C34 derivatives. By taking a blood sample from the host at different times, one may determine whether C34 peptide has become bonded to the long-lived blood components in sufficient amount to be therapeutically active and, thereafter, the level of C34 in the blood. If desired, one may also determine to which of the blood components C34 is covalently bonded. Monitoring may also take place by using assays of C34 activity, HPLC-MS or antibodies directed to C34.

The following examples are provided to illustrate preferred embodiments of the invention and shall by no means be construed as limiting its scope.

The present C34 derivatives can be administered to patients according to the methods described below and other methods known in the art. Effective therapeutic dosages of the present C34 derivatives may be determined through procedures well known by those in the art and will take into consideration any concerns over potential toxicity of C34.

The present C34 derivative can also be administered prophylactically to previously uninfected individuals. This can be advantageous in cases where an individual has been subjected to a high risk of exposure to a virus, as can occur when individual has been in contact with an infected individual where there is a high risk of viral transmission. This can be expecially advantageous where there is known cure for the virus, such as the HIV virus. As an example, prophylactic administration of a C34 derivative would be advantageous in a situation where a health care worker has been exposed to blood from an HIV-infected individual, or in other situations where an individual engaged in high-risk activities that potentially expose that individual to the HIV virus.

The invention having been fully described can be further appreciated and understood with reference to the following non-limiting examples.

General

Unless stated otherwise, the synthesis of each C34 derivative was performed using an automated solid-phase procedure on a Symphony Peptide Synthesizer with manual intervention during the generation of the derivative. The synthesis was performed on Fmoc-protected Ramage amide linker resin, using Fmoc-protected amino acids. Coupling was achieved by using O-benzotriazol-1-yl-N,N,N',N'-tetramethyl-uronium hexafluorophosphate (HBW) as activator in N,N-dimethylformamide (DMF) solution and diisopropyl-ethylamine (IDEA) as base. The Fmoc protective group was removed using 20% piperidine/DMF. When needed, a Boc-protected amino acid was used at the N-terminus in order to generate the free $N_\alpha$-terminus after the peptide is cleaved from resin. All amino acids used during the synthesis possess the L-stereochemistry. Glass reaction vessels were used during the synthesis.

EXAMPLE 1

Compound of Formula I

Step 1: The example describes the solid phase peptide synthesis of the compound on a 100 μmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Aloc)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Met-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol ($^i$PrOH).

Step 4: The peptide was cleaved from the resin using 85% TFA/5% triisopropyl-silane (TIPS)/5% thioanisole and 5% phenol, followed by precipitation by dry-ice cold Et$_2$O (Step 4).

EXAMPLE 2

Compound of Formula H

Step 1: The example describes the solid phase peptide synthesis of the compound on a 100 μmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Lys(Aloc)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Trp(Boc)-OH, Fmoc-Glu(tBu)-OH, Fmoc-Met-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol ($^i$PrOH).

Step 4: The peptide was cleaved from the resin using 85% TFA/5% TIS/5% thioanisole and 5% phenol, followed by precipitation by dry-ice cold Et$_2$O (Step 4).

EXAMPLE 3

Compound of Formula III

Step 1: The example describes the solid phase peptide synthesis of the compound on a 100 μmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Ser(tBu)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-Thr(tBu)-OH, Fmoc-Tyr(tBu)-OH, Fmoc-Lys(Aloc)-OH, Fmoc-Asn(Trt)-OH, Fmoc-Ine-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Met-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N, 1, N-tetramethyl-uronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol (iPrOH).

Step 4: The peptide was cleaved from the resin using 85% TFA/5% TIS/5% thioanisole and 5% phenol, followed by precipitation by dry-ice cold Et$_2$O (Step 4).

EXAMPLE 4

Compound of Formula IV

Step 1: The example describes the solid phase peptide synthesis of the compound on a 100 μmole scale. The following protected amino acids were sequentially added to resin: Fmoc-Leu-OH, Fmoc-Leu-OH Fmoc-Glu(tBu)-OH, Fmoc-Gln(Trt)-OH, Fmoc-Glu(tBu)-OH, Fmoc-Asn(Trt)-OH, Fmoc-Ser(tBu)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-Thr(tBu)-OH, Fmoc-Tyr(tBu)-OH, Fmoc-Asn(Trt)-OH, Fmoc-Lys(Aloc)-OH, Fmoc-Ile-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Met-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol ($^i$PrOH).

Step 4: The peptide was cleaved from the resin using 85% TFA/5% TIS/5% thioanisole and 5% phenol, followed by precipitation by dry-ice cold Et$_2$O (Step 4).

EXAMPLE 5

Compound of Formula V

Step 1: The example describes the solid phase peptide synthesis of the compound on a 100 μmole scale. The following protected amino acids were sequentially added to resin: Fmoc-Lys(Aloc)-OH, Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Ser(tBu)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Met-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethyl-amine (DIEA).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the 3-maleimido-propionic acid (Step 3). Between every coupling, the resin was washed 3 times with N,N-dimethylformamide (DMF) and 3 times with isopropanol ($^i$PrOH).

Step 4: The peptide was cleaved from the resin using 85% TFA/5% TIS/5% thioanisole and 5% phenol, followed by precipitation by dry-ice cold Et$_2$O (Step 4).

EXAMPLE 6

Compound of Formula VI

Step 1: The example describes the solid phase peptide synthesis of the compound on a 100 μmole scale. The following protected amino acids were sequentially added to resin: Fmoc-Lys(Aloc)-OH, Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Ser(tBu)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Met-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N, N,N'-tetramethyl-uronium hexafluorophosphate (HBTU) and diisopropylethyl-amine (DIEA).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the Fmoc-AEEA-OH and the 3-maleimidopropionic acid (Step 3). Between every coupling, the resin was washed 3 times with N,N-dimethylformamide (DMF) and 3 times with isopropanol ($^i$PrOH).

Step 4: The peptide was cleaved from the resin using 85% TFA/5% TIS/5% thioanisole and 5% phenol, followed by precipitation by dry-ice cold Et$_2$O (Step 4).

EXAMPLE 7

Compound of Formula VII

Step 1: The example describes the solid phase peptide synthesis of the compound on a 100 μmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Ser(tBu)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Met-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The synthesis was continued for the addition of the 3-maleimidopropionic acid (Step 2). Between every coupling, the resin was washed 3 times with N,N-dimethylformamide (DMF) and 3 times with isopropanol (<sup>i</sup>PrOH).

Step 3: The peptide was cleaved from the resin using 85% TFA/5% TIS/5% thioanisole and 5% phenol, followed by precipitation by dry-ice cold Et$_2$O (Step 3).

EXAMPLE 8

Compound of Formula VIII

Step 1: The example describes the solid phase peptide synthesis of the compound on a 100 μmole scale. The following protected amino acids were sequentially added to resin: Fmoc-Leu-OH, Fmoc-Leu-OH, Fmoc-Glu(tBu)-OH, Fmoc-Gln(Trt)-OH, Fmoc-Glu(tBu)-OH, Fmoc-Asn(Trt)-OH, Fmoc-Ser(tBu)-OH, Fmoc-Glu(tBu)-OH, Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-Thr(tBu)-OH, Fmoc-Tyr(tBu)-OH, Fmoc-Asn(Trt)-OH, Fmoc-Asn(Trt)-OH, Fmoc-Ile-OH, Fmoc-Glu(tBu)-OH, Fmoc-Arg(Pbf)-OH, Fmoc-Asp(tBu)-OH, Fmoc-Trp(Boc)-OH, Fmoc-Glu(tBu)-OH, Fmoc-Met-OH, Fmoc-Trp(Boc)-OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DIEA).

Step 2: The synthesis was continued for the addition of the FMOC-AEEA-OH and the 3-maleimidopropionic acid (Step 2). Between every coupling, the resin was washed 3 times with N,N-dimethylformamide (DMF) and 3 times with isopropanol (<sup>i</sup>PrOH).

Step 3: The peptide was cleaved from the resin using 85% TFA/5% TIS/5% thioanisole and 5% phenol, followed by precipitation by dry-ice cold Et$_2$O (Step 3).

Cellular Anti-HIV Assay (MTT Assay)

The antiviral activity was determined as described in *Journal of Virological Methods*, 1988, 20, 309-321. Briefly, various concentrations of the test compound were brought into each well of a flat-bottom microtiter plate. Subsequently, HIV strain (HIV-1 IIIB) and MT-4 cells were added to a final concentration of 200 CCID$_{50}$/well and 30,000 cells/well, respectively. In order to determine the toxicity of the test compound, mock-infected cell cultures containing an identical compound concentration range, were incubated in parallel with the HIV-infected cell cultures. After 5 days of incubation (37° C., 5% CO$_2$), the viability of the cells was determined by the tetrazolium colorimetric MTT method. The results of both assays appear in Table 2 below.

TABLE 2

| Compound | Comment | Antiviral assay IC50 (μM) |
|---|---|---|
| Native C34 | — | 0.0064 |
| Formula I | quenched | 0.0063 |
|  | HSA conjugate | 0.1149 |
| Formula II | quenched | 0.0052 |
|  | HSA conjugate | 0.0200 |
| Formula III | quenched | 0.0077 |
|  | HSA conjugate | 0.0232 |
| Formula IV | quenched | 0.0048 |
|  | HSA conjugate | 0.0207 |
| Formula V | quenched | 0.0072 |
|  | HSA conjugate | 0.439 |
| Formula VI | quenched | 0.0047 |
|  | HSA conjugate | 0.0253 |
| Formula VII | quenched | 0.3171 |
|  | HSA conjugate | 0.6602 |
| Formula VIII | quenched | 0.0015 |
|  | HSA conjugate | 0.0175 |

While the invention has been described in connection with specific embodiments thereof, it will be understood that it is capable of further modifications, and this application is intended to cover any variations, uses or adaptations of the invention following, in general, the principles of the invention, and including such departures from the present description as come within known or customary practice within the art to which the invention pertains, and as may be applied to the essential features hereinbefore set forth, and as follows in the scope of the appended claims.

What is claimed is:

1. A compound of Formulae I-VIII corresponding in order of appearance to SEQ ID NOS: 2, 3, 4, 5, 6, 7, 8 and 9:

I

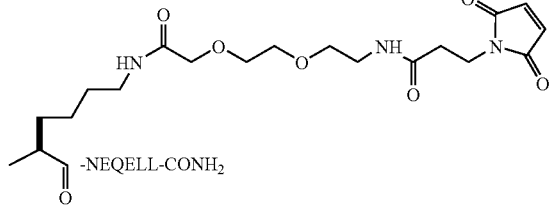

II

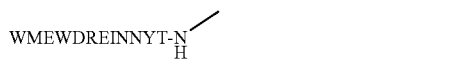

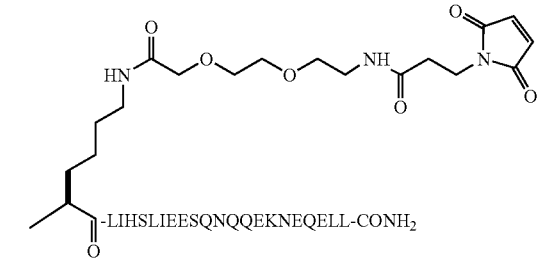

III

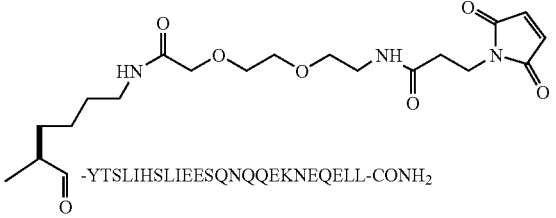

IV

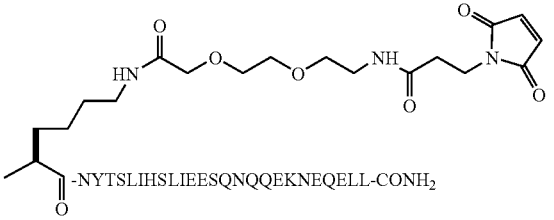

V

WMEWDREINNYTSLIHSLIEESQNQQEKNEQELL-N
H

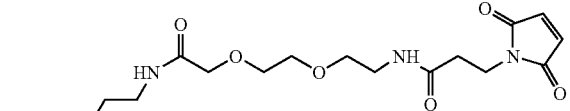

—CONH₂

VI

WMEWDREINNYTSLIHSLIEESQNQQEKNEQELL-

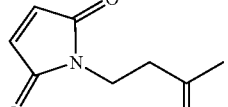

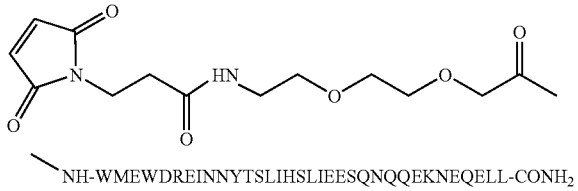

—CONH₂

VII

HN-WMEWDREINNYTSLIHSLIEESQNQQEKNEQELL-CONH₂

VIII

NH-WMEWDREINNYTSLIHSLIEESQNQQEKNEQELL-CONH₂ or a compound according to any of Formulae I-VI further comprising an N-terminal acetyl group.

2. The compound of claim 1, which is conjugated to a blood component in vitro.

3. The compound of claim 2, wherein the compound is reactive with a thiol group on an albumin.

4. A pharmaceutical composition comprising the compound as claimed in any of claim 1, 2 or 3 in combination with a pharmaceutically acceptable carrier.

5. A composition as claimed in claim 4 for inhibiting the activity of HIV.

6. A method for inhibiting the activity of HIV in a subject comprising administering to the subject an effective amount of the compound as claimed in claim 1, alone or in combination with a pharmaceutically acceptable carrier.

7. A conjugate comprising the compound as claimed in claim 1 covalently bonded to a blood component.

8. A method for extending the in vivo half-life of the compound as claimed in claim 1, the method comprising covalently bonding the compound to a blood component.

9. A composition as claimed in claim 4 for inhibiting the fusogenic activity of HIV.

10. A method for inhibiting the activity of HIV in a subject comprising administering to the subject an effective amount of the conjugate as claimed in claim 7, alone or in combination with a pharmaceutically acceptable carrier.

11. The conjugate of claim 7, wherein the blood component is selected from the group consisting of albumin, transferrin, ferritin and immunoglobulins.

12. The conjugate of claim 11, wherein the blood component is albumin.

13. The conjugate of claim 12, wherein the compound is conjugated to Cys[34] of albumin via a stable bond.

14. The compound of claim 1, which is conjugated to a blood component in vivo.

15. The compound of claim 14, wherein the compound is reactive with a thiol group on an albumin.

16. The compound of claim 15, wherein the compound is reactive with $Cys^{34}$ of albumin to form a stable covalent bond.

17. The compound of claim 3, wherein the compound is reactive with $Cys^{34}$ of albumin to form a stable covalent bond.

18. The compound of claim 17, wherein the compound is loaded to albumin in a 1:1 molar ratio.

19. The method of claim 6, wherein the compound is administered by a method selected from the group consisting of intravascular, intramuscular, and subcutaneously.

20. The method of claim 19, wherein the compound is administered at a concentration of 1 pg/ml to 50 mg/ml.

21. The method of claim 10, wherein the conjugate is administered by a method selected from the group consisting of intravascular, intramuscular, and subcutaneously.

22. The method of claim 21, wherein the conjugate is administered at a concentration of 1 pg/ml to 50 mg/ml.

23. A pharmaceutical composition comprising a conjugate as in any of claim 7, 11 or 13 in combination with a pharmaceutically acceptable carrier.

24. A method for inhibiting the fusogenic activity of HIV in a subject, comprising administering to the subject an effective amount the conjugate as in claim 7, alone or in combination with a pharmaceutically acceptable carrier.

25. The compound of claim 1, which is the compound of Formula I, or a compound according to Formula I further comprising an N-terminal acetyl group.

26. The compound of claim 1, which is the compound of Formula II, or a compound according to Formula II further comprising an N-terminal acetyl group.

27. The compound of claim 1, which is the compound of Formula III, or a compound according to Formula III further comprising an N-terminal acetyl group.

28. The compound of claim 1, which is the compound of Formula IV, or a compound according to Formula IV further comprising an N-terminal acetyl group.

29. The compound of claim 1, which is the compound of Formula V, or a compound according to Formula V further comprising an N-terminal acetyl group.

30. The compound of claim 1, which is the compound of Formula VI, or a compound according to Formula VI further comprising an N-terminal acetyl group.

31. The compound of claim 1, which is the compound of Formula VII.

32. The compound of claim 1, which is the compound of Formula VIII.

33. The compound of claim 25, which is conjugated to a blood component in vivo or in vitro.

34. The compound of claim 26, which is conjugated to a blood component in vivo or in vitro.

35. The compound of claim 27, which is conjugated to a blood component in vivo or in vitro.

36. The compound of claim 28, which is conjugated to a blood component in vivo or in vitro.

37. The compound of claim 29, which is conjugated to a blood component in vivo or in vitro.

38. The compound of claim 30, which is conjugated to a blood component in vivo or in vitro.

39. The compound of claim 31, which is conjugated to a blood component in vivo or in vitro.

40. The compound of claim 32, which is conjugated to a blood component in vivo or in vitro.

41. The compound of claim 33, wherein the compound is reactive with a thiol group on the blood component, and wherein the blood component is albumin.

42. The compound of claim 34, wherein the compound is reactive with a thiol group on the blood component, and wherein the blood component is albumin.

43. The compound of claim 35, wherein the compound is reactive with a thiol group on the blood component, and wherein the blood component is albumin.

44. The compound of claim 36, wherein the compound is reactive with a thiol group on the blood component, and wherein the blood component is albumin.

45. The compound of claim 37, wherein the compound is reactive with a thiol group on the blood component, and wherein the blood component is albumin.

46. The compound of claim 38, wherein the compound is reactive with a thiol group on the blood component, and wherein the blood component is albumin.

47. The compound of claim 39, wherein the compound is reactive with a thiol group on the blood component, and wherein the blood component is albumin.

48. The compound of claim 40, wherein the compound is reactive with a thiol group on the blood component, and wherein the blood component is albumin.

49. A method for inhibiting the activity of HIV in a subject comprising administering to the subject an effective amount of the compound as claimed in claim 41, alone or in combination with a pharmaceutically acceptable carrier.

50. A method for inhibiting the activity of HIV in a subject comprising administering to the subject an effective amount of the compound as claimed in claim 42, alone or in combination with a pharmaceutically acceptable carrier.

51. A method for inhibiting the activity of HIV in a subject comprising administering to the subject an effective amount of the compound as claimed in claim 43, alone or in combination with a pharmaceutically acceptable carrier.

52. A method for inhibiting the activity of HIV in a subject comprising administering to the subject an effective amount of the compound as claimed in claim 44, alone or in combination with a pharmaceutically acceptable carrier.

53. A method for inhibiting the activity of HIV in a subject comprising administering to the subject an effective amount of the compound as claimed in claim 45, alone or in combination with a pharmaceutically acceptable carrier.

54. A method for inhibiting the activity of HIV in a subject comprising administering to the subject an effective amount of the compound as claimed in claim 46, alone or in combination with a pharmaceutically acceptable carrier.

55. A method for inhibiting the activity of HIV in a subject comprising administering to the subject an effective amount of the compound as claimed in claim 47, alone or in combination with a pharmaceutically acceptable carrier.

56. A method for inhibiting the activity of HIV in a subject comprising administering to the subject an effective amount of the compound as claimed in claim 48, alone or in combination with a pharmaceutically acceptable carrier.

57. The method of any of claims 49-56, wherein the compound is administered by a method selected from the group consisting of intravascular, intramuscular, and subcutaneously.

58. A conjugate comprising the compound as claimed in claim 41 covalently bonded to the blood component.

59. A conjugate comprising the compound as claimed in claim 42 covalently bonded to the blood component.

60. A conjugate comprising the compound as claimed in claim 43 covalently bonded to the blood component.

61. A conjugate comprising the compound as claimed in claim 44 covalently bonded to the blood component.

62. A conjugate comprising the compound as claimed in claim 45 covalently bonded to the blood component.

63. A conjugate comprising the compound as claimed in claim 46 covalently bonded to a blood component.

64. A conjugate comprising the compound as claimed in claim 47 covalently bonded to a blood component.

65. A conjugate comprising the compound as claimed in claim 48 covalently bonded to a blood component.

66. A method for inhibiting the activity of HIV in a subject comprising administering to the subject an effective amount of the conjugate as claimed in claim 58, alone or in combination with a pharmaceutically acceptable carrier.

67. A method for inhibiting the activity of HIV in a subject comprising administering to the subject an effective amount of the conjugate as claimed in claim 59, alone or in combination with a pharmaceutically acceptable carrier.

68. A method for inhibiting the activity of HIV in a subject comprising administering to the subject an effective amount of the conjugate as claimed in claim 60, alone or in combination with a pharmaceutically acceptable carrier.

69. A method for inhibiting the activity of HIV in a subject comprising administering to the subject an effective amount of the conjugate as claimed in claim 61, alone or in combination with a pharmaceutically acceptable carrier.

70. A method for inhibiting the activity of HIV in a subject comprising administering to the subject an effective amount of the conjugate as claimed in claim 62, alone or in combination with a pharmaceutically acceptable carrier.

71. A method for inhibiting the activity of HIV in a subject comprising administering to the subject an effective amount of the conjugate as claimed in claim 63, alone or in combination with a pharmaceutically acceptable carrier.

72. A method for inhibiting the activity of HIV in a subject comprising administering to the subject an effective amount of the conjugate as claimed in claim 64, alone or in combination with a pharmaceutically acceptable carrier.

73. A method for inhibiting the activity of HIV in a subject comprising administering to the subject an effective amount of the conjugate as claimed in claim 65, alone or in combination with a pharmaceutically acceptable carrier.

\* \* \* \* \*